(12) United States Patent
Nace (10) Patent No.: US 9,089,403 B2
(45) Date of Patent: *Jul. 28, 2015

(54) KNEE ORTHOSIS WITH HINGED SHIN AND THIGH CUFFS

(71) Applicant: MEDICAL ALLIANCE SA, San Jose (CR)

(72) Inventor: Richard A. Nace, San Jose (CR)

( * ) Notice: Subject to any disclaimer, the term of this patent is extended or adjusted under 35 U.S.C. 154(b) by 202 days.

This patent is subject to a terminal disclaimer.

(21) Appl. No.: 13/648,515

(22) Filed: Oct. 10, 2012

(65) Prior Publication Data

US 2013/0041300 A1    Feb. 14, 2013

Related U.S. Application Data

(63) Continuation-in-part of application No. 12/469,671, filed on May 20, 2009, now Pat. No. 8,308,669.

(51) Int. Cl.
*A61F 5/01* (2006.01)

(52) U.S. Cl.
CPC ....... *A61F 5/0125* (2013.01); *A61F 2005/0165* (2013.01); *A61F 2005/0172* (2013.01); *A61F 2005/0179* (2013.01)

(58) Field of Classification Search
CPC ................ A61F 5/0123; A61F 5/0125; A61F 2005/0179
USPC ..................................... 602/16, 23, 26; 601/5
See application file for complete search history.

(56) References Cited

U.S. PATENT DOCUMENTS

| | | | |
|---|---|---|---|
| 4,370,977 A * | 2/1983 | Mauldin et al. ................. | 602/16 |
| 4,503,846 A * | 3/1985 | Martin ........................... | 602/16 |
| 4,606,542 A | 8/1986 | Segal | |
| 4,865,024 A * | 9/1989 | Hensley et al. ................. | 602/16 |
| 4,991,571 A | 2/1991 | Kausek | |
| 5,415,625 A * | 5/1995 | Cassford et al. ................ | 602/26 |
| 5,514,081 A * | 5/1996 | Mann .............................. | 602/20 |
| RE37,209 E * | 6/2001 | Hensley et al. ................. | 602/26 |
| 6,527,733 B1 * | 3/2003 | Ceriani et al. .................. | 602/16 |
| 7,048,704 B2 * | 5/2006 | Sieller et al. ................... | 602/16 |
| 7,410,472 B2 * | 8/2008 | Yakimovich et al. ........... | 602/16 |
| 2002/0133108 A1 | 9/2002 | Jagodzinski | |

* cited by examiner

*Primary Examiner* — Alireza Nia
*Assistant Examiner* — Raymond E Harris
(74) *Attorney, Agent, or Firm* — Larson & Larson, P.A.; Justin P. Miller; Patrick A. Reid (57) ABSTRACT

A disclosed knee orthosis has two vertical struts positioned on opposed sides of a knee joint in a generally parallel relationship. Each vertical strut has a hinge member located at a general middle portion; each vertical strut has a top and bottom end portion. An upper thigh cuff attaches at opposed ends to the upper end portions of the two vertical struts whereas a lower shin cuff attaches at opposed ends to the lower end portions. The lower shin cuff has a pair of hinges located proximal to the shin cuff opposed ends for permitting the shin cuff to pivot downwardly away from a shin of a person wearing the knee orthosis. An alternate embodiment employs hinges located proximal to the thigh cuff opposed ends for permitting the thigh cuff to pivot upwardly away from a thigh of a person when the same motion is performed.

20 Claims, 8 Drawing Sheets

KNEE ORTHOSIS WITH HINGED SHIN AND THIGH CUFFS

CROSS-REFERENCE TO RELATED APPLICATION

This application is a continuation-in-part of U.S. patent application Ser. No. 12/469,671, filed May 20, 2009, the disclosure of which is hereby incorporated by reference.

FIELD

The invention relates to a knee orthosis. More particularly, it refers to a pre-operative, post operative knee orthosis for stabilizing a knee joint of a person before or after surgery or after injury thereto, that applies an adjustable corrective and therapeutic force to the knee joint and surrounding muscles above and below the knee and which also removes pressure from a lower shin cuff of the knee orthosis when a patient using the novel knee orthosis of this present invention flexes the knee joint or performs a body squatting motion through rotation about a shin cuff hinge.

Background

Orthosis devices and appliances commonly referred to as "orthotics," are known in the prior art and have been utilized for many years by orthotists (a maker and fitter of orthotics), physical therapists, and occupational therapists to assist in the rehabilitation of a patient's joints and associated limbs or adjacent skeletal parts of the patient's body related to a variety of conditions. An early example can be seen in U.S. Pat. No. 3,581,741 to Rosman, which discloses a knee brace comprising an upper rigid body portion and a lower rigid body portion pivotably coupled together on the lateral side in a manner so that they may pivot relative to each other about an axis generally perpendicular to the zone of overlap and may slide relative to each other in all radial directions generally parallel to the zone of overlap.

Webster's New College Dictionary defines "orthotics" as a branch of mechanical medical science that deals with the support and bracing of weak or ineffective joints or muscles. The word "ortho" actually comes from Greek and means "to straighten." Orthotics are used to support, straighten, and stabilize affected joints and assist to correct normal human function as closely as possible. Orthotics used as knee braces have typically been designed to support and protect the knee joint that is associated with a variety of knee joint conditions, for alleviating pain associated with joint movement at the particular location being treated or for immobilizing the knee joint so that movement thereof in either the medial or lateral directions or rotation of the knee is eliminated or at least significantly reduced.

Repetitive use of a joint, such as the knee, over time tends to reduce the stability of the knee. In cases of injury through accident or sports related causes, instability of the knee can be exacerbated and worsened to the point that without immobilization or support of the knee joint by an orthotic, a person cannot bear the weight of their own body upon the knee joint. Or to do so results in great pain, which is usually treated with pain medications that can be addictive and hard on the liver and other important organs of the body. Further, when there is a lack of movement of a patient due to knee instability, a sedentary lifestyle is usually taken up, which can result in a reduction of body energy, weight gain, atrophied muscles concentrated around the knee joint, and a general depression of mental state due to the lack of ability of the person to be self-sufficient and mobile.

Therefore, it can be plainly seen that knee orthotics of all types are useful if they assist a person in returning to a more normal lifestyle or at least one that is significantly less sedentary when compared to the immobile person with an instable knee. It can be said that proper use of the knee joints is essential to complete body health and a proper state of mind.

It is well known, as complaints are abundant, that not all knee orthotics or braces that stabilize the knee are comfortable to wear. In fact, most knee orthotics apply unwanted pressure to the thigh and the shin of the patient when the patient walks, squats, or flexes the knee joint. This is because all prior art knee orthotics are typically made from very hard and rigid materials that do not flex and move with the changing conditions of the body (i.e., expansion and contraction of the leg musculature). Such areas of change include the knee joint area and the upper and lower leg when the patient is walking, flexing, or squatting. This can be particularly seen with the shin cuff that applies a great amount of pressure against the shin of the patient when the patient squats. This pressure, therefore, discourages the patient from performing any squatting action, which in turns encourages the patient to remain sedentary, resulting in the degradation of physical and mental state.

Further, prior art knee orthotics do not apply therapeutic and corrective forces to the knee joint area and the surrounding leg musculature area. Such is needed in combination with a flexible and pliable brace that incorporates a system for reducing or eliminating pressure placed against the shin of the patient when the patient walks or flexes the knee joint or when he squats his body. This can also include alone or together a system for reducing or eliminating pressure placed against the thigh of the patient when the patient walks or flexes the knee joint or when he squats. The specific elements that accomplish such pressure elimination include, in the present invention, flexible and pliable materials for one or both the shin or thigh cuffs, and hinged shin and thigh cuffs that permit rotation from a 90 degree position to a degree of at least 45 degrees, if not further.

Summary

The knee orthosis of the present invention provides all of the advantages needed, which are mentioned above and that are currently deficient and wholly missing from the prior art. The present knee orthosis is used and indicated for increased medial, lateral, and rotational support and control of the knee joint following injury to, or reconstruction of, the anterior cruciate ligament (ACL) and posterior cruciate ligament (PCL), or protection of the collateral ligament of the knee. The present invention provides increased support for patients who have continued symptoms of significant knee instability such as giving way, which may be due to poor quadriceps or hamstring strength (i.e., hemiplegia), or for patients who have a desire to quickly resume activities after knee surgery. The present knee orthosis is also useful after total knee replacement or high tibia osteotomy.

To provide the above set forth benefits and improvements over the prior art, the present knee orthosis device includes two vertical struts, positioned on opposed sides of a knee joint in a generally parallel relationship, wherein each vertical strut has a hinge member located at a general middle portion thereof, and further wherein each vertical strut has a top and bottom end portion. Both polycentric and uni-centric hinges can be employed for the two hinges members, in any combination thereof. An upper thigh cuff attached at opposed ends to the upper end portions of the two vertical struts provides a means to secure the knee orthosis to the thigh of the patient. A secondary thigh strap is also employed to provide additional securing means and is positioned slightly below the thigh cuff. The thigh cuff is positioned posterior to the thigh, whereas the secondary thigh strap and a strap used to secure the thigh cuff are both positioned anterior to the thigh of the patient.

A shin cuff attaches at opposed ends to the lower end portions of the two vertical struts and is positioned anterior to the shin. The shin cuff has a strap member that wraps around the back of the shin of the patient for securing it to the patient's shin. A secondary shin strap is positioned slightly above the shin cuff but is positioned on the posterior side of the shin area of the patient.

The lower shin cuff has a pair of hinges located proximal to the shin cuff opposed ends and left and right vertical strut lower end portions for permitting the shin cuff to pivot downwardly away from a shin of a person wearing the knee orthosis when a person flexes the knee or performs a squatting motion thereby reducing or eliminating unwanted pressure that is usually applied to the shin of a patient of a person when they flex the knee, walk or squat. The shin cuff can pivot upwards of 60-75 degrees.

The novel knee orthosis of the present invention also employs a plurality of air bladders used as therapeutic 7 and corrective force elements for the device. The air bladders are removably positionable along inner surfaces of the two vertical struts and hinges. Any number from one to six air bladders can be employed such that force can be applied on both sides of the knee joint, at the knee joint, directly above the knee joint on the inner and outer thigh area and directly below the knee joint on the inner and outer shin area. When employed the air bladders also provide additional stabilization to the knee, prevent brace slippage and provide an extra degree of comfort to patient.

The novel knee orthosis also employs elastic thigh and cuff cushion members positioned along the inner surfaces of the thigh and shin cuff, respectively, for providing more comfort and support. The elasticity of these cushions allows them to bend and flex with the movements of the patient but return to their stable positions after movement by the patient such that the patient's knee joint is continuously stabilized regardless of the movement made by the patient using the knee orthosis of the present invention.

In a first alternate embodiment, the upper thigh cuff also has a pair of hinges located proximal to the thigh cuff opposed ends and left and right vertical strut upper end portions for permitting the thigh cuff to pivot upwardly away from a thigh of a person wearing the knee orthosis when a person flexes the knee or performs any other motion thereby reducing or eliminating unwanted pressure that is usually applied to the thigh of a patient of a person when they flex the knee, walk or squat. The thigh cuff can pivot upwards of 60-75 degrees or more.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Throughout the following detailed description the same reference numerals refer to the same elements in all figures.

Figure 1:
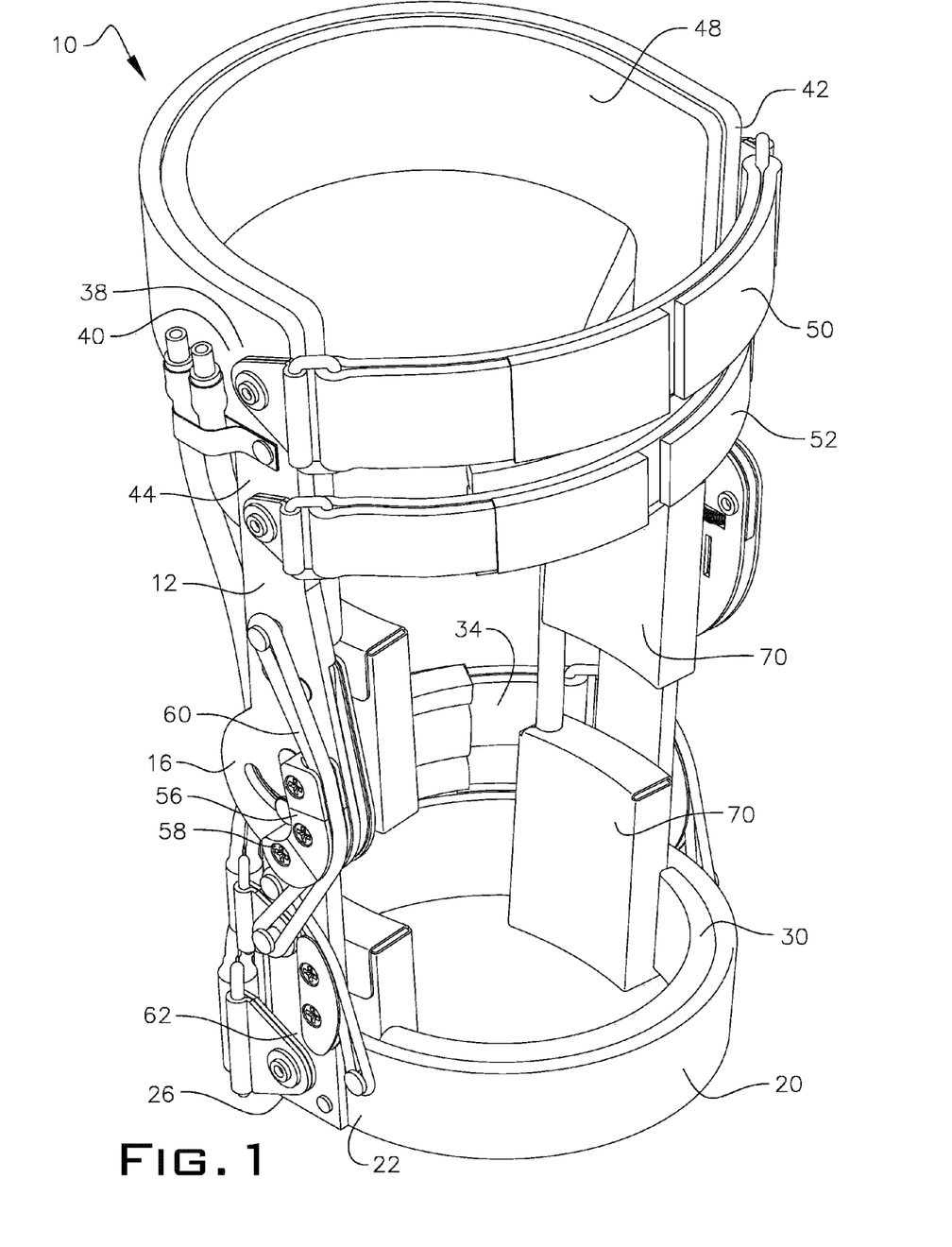
FIG. 1 is a left side perspective view of the knee orthosis of the present invention.
Figure 2:
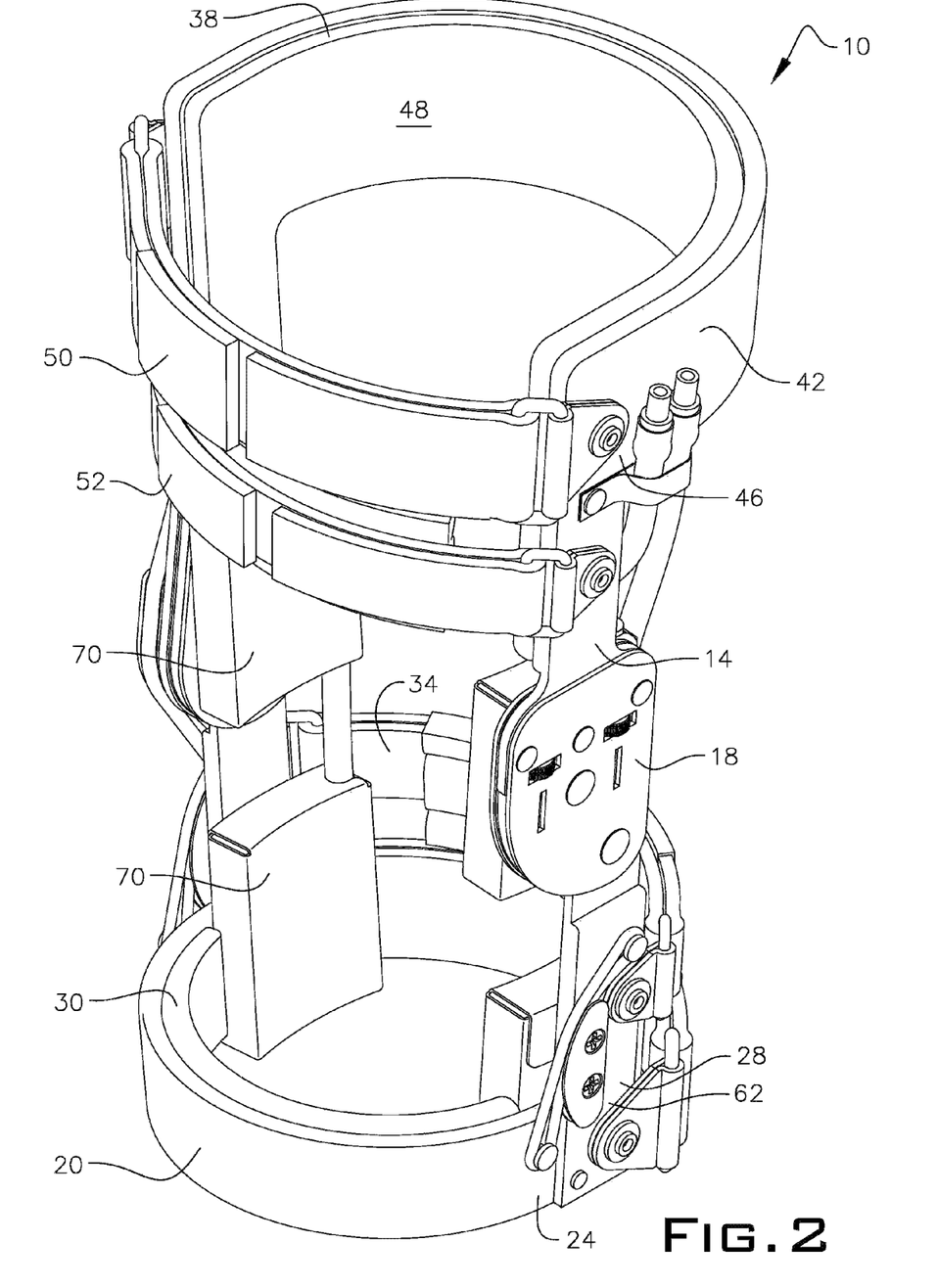
FIG. 2 is a right side perspective view of the knee orthosis of the present invention.

Referring to FIGS. 1 and 2, a knee orthosis 10 of the present is shown. As shown, knee orthosis 10 has a left side and right side vertical strut, 12 and 14, respectively. Struts 12 and 14 are generally parallel and when knee orthosis 10 is employed on a patient, run along medial and lateral sides of a knee joint and thigh and shin area of the patient. Each strut has its own hinge 16 and 18 positioned intermediate top and bottom portions of struts 12 and 14 such that knee orthosis 10 pivots about said hinges when the knee joint of the patient is flexed. In the embodiment shown in FIGS. 1 and 2, hinge 16 is a polycentric hinge and hinge 18 is a uni-centric hinge. However, nothing herein limits the use of knee orthosis to this embodiment shown and described herein in this preferred embodiment could be employed. In fact, any combination of hinges could be employed.

Figure 3:
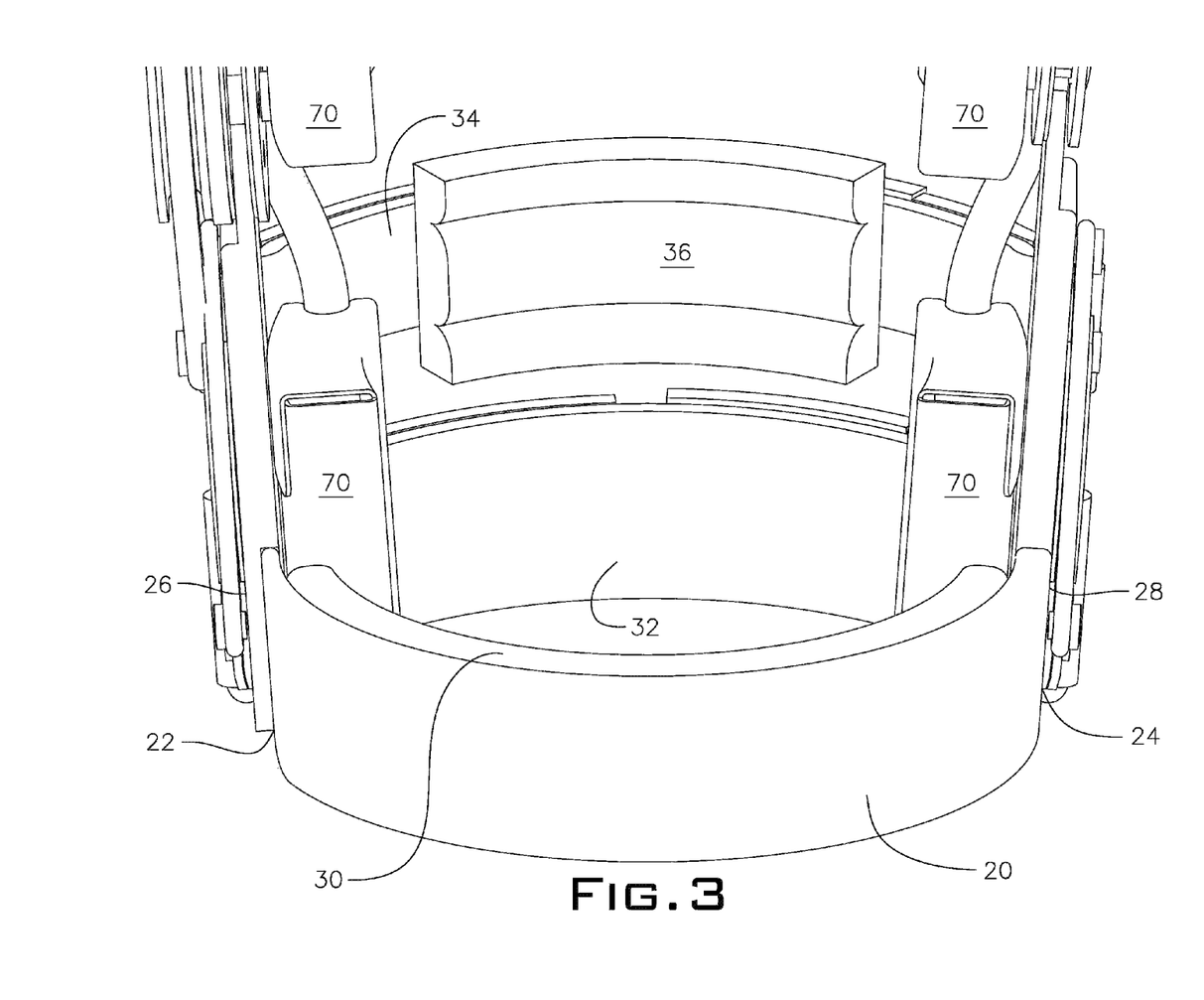
FIG. 3 is a front view of the knee orthosis of the present invention illustrating the shin cuff located at a lower end of the knee orthosis.

Referring to FIG. 3, and also with continuing reference to FIGS. 1 and 2, an anterior positioned shin cuff 20 is shown that has opposed ends 22 and 24. Shin cuff opposed ends 22 and 24 attach to lower ends 26 and 28 of left and right side vertical struts 12 and 14. Attached along an inner surface (not shown) of shin cuff 20 is a flexible shin cushion pad 30 which is removably attached to said shin cuff 20 inner surface. Shin cuff cushion 30 is very pliable, with a shape capable of being manipulated and then able to return to its normal resting state, as shown in FIG. 3. It is attached to shin cuff 20 inner surface by hook and loop material.

With continuing reference to FIG. 3, it is shown that shin cuff 20 has a shin cuff strap 32 that wraps behind the shin of a patient for securing thereto. Further, a secondary shin strap 34, with a positionable cushion pad 36, is positioned slightly above shin cuff strap 32 and is used to provide extra securing means for the knee orthosis 10 to the patient. Both shin cuff strap 32 and secondary shin strap 34 each have opposed ends which loop through D-rings (see FIGS. 5 and 6) and then attach to themselves by hook and loop material.

Figure 4:
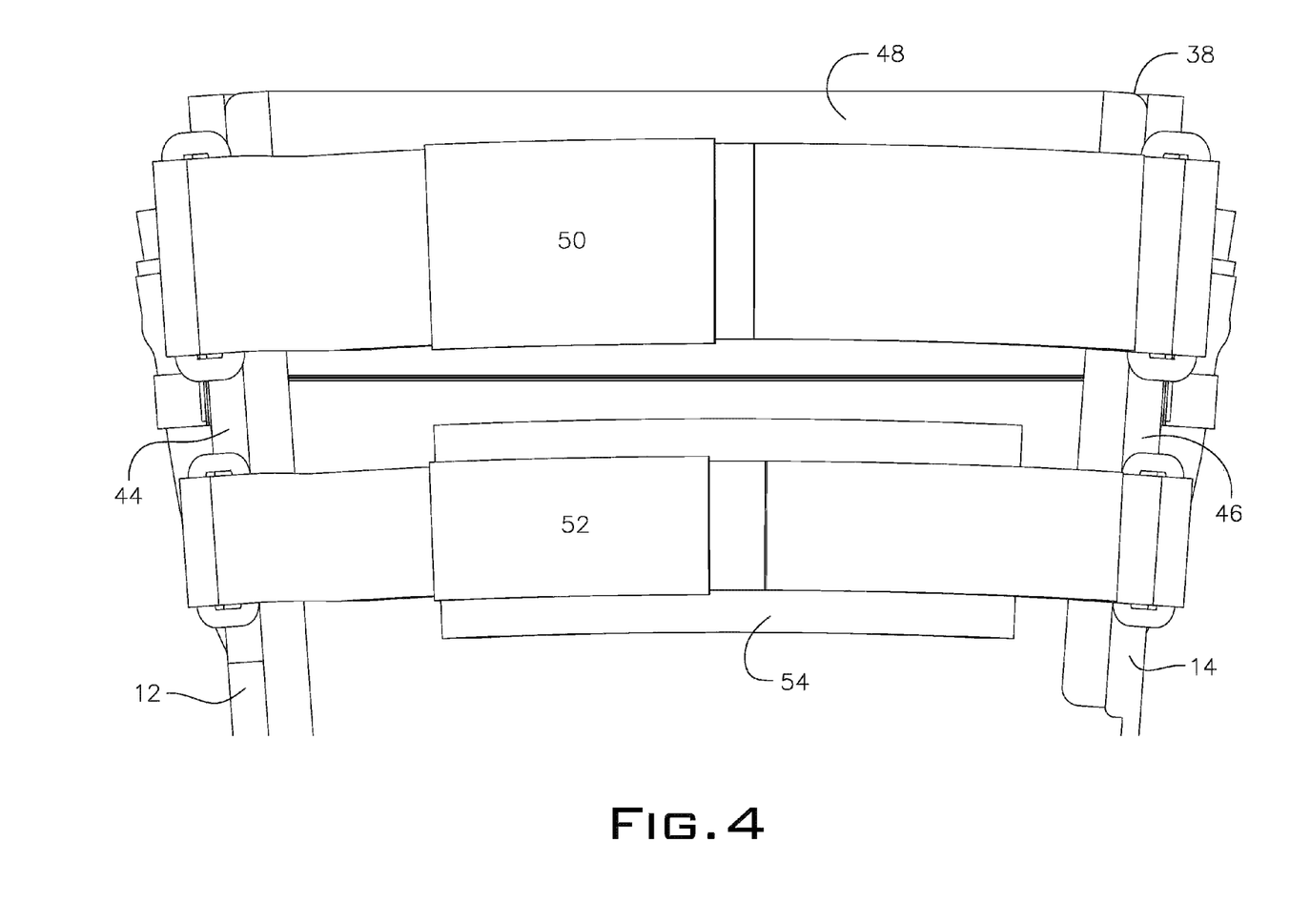
FIG. 4 is a front view of the knee orthosis of the present invention illustrating the thigh cuff located at an upper end of the knee orthosis.

Referring now to FIG. 4, and also with continuing reference to FIGS. 1 and 2, a posterior thigh cuff 38 is shown that has opposed ends 40 and 42. Thigh cuff opposed ends 40 and 42 attach to upper ends 44 and 46 of left and right side vertical struts 12 and 14. Attached along an inner surface (not shown) of thigh cuff 38 is a flexible thigh cushion pad 48 that is removably attached to thigh cuff 38 inner surface. Thigh cuff cushion pad 48 is very pliable, with a shape capable of being manipulated and then able to return to its normal resting state, as shown in FIG. 4. It is attached to thigh cuff 38 inner surface by hook and loop material.

With continuing reference to FIG. 4, it is shown that thigh cuff 38 has a thigh cuff strap 50 which wraps in front of the thigh of a patient for securing thereto. Further, a secondary thigh strap 52, with a positionable cushion pad 54 is positioned slightly below thigh cuff strap 50 and is used to provide extra securing means for the knee orthosis 10 to the patient. Both thigh cuff strap 50 and secondary thigh strap 52 each have opposed ends which loop through D-rings (see FIGS. 1 and 2) and then attach to themselves by hook and loop material.

Figure 5:
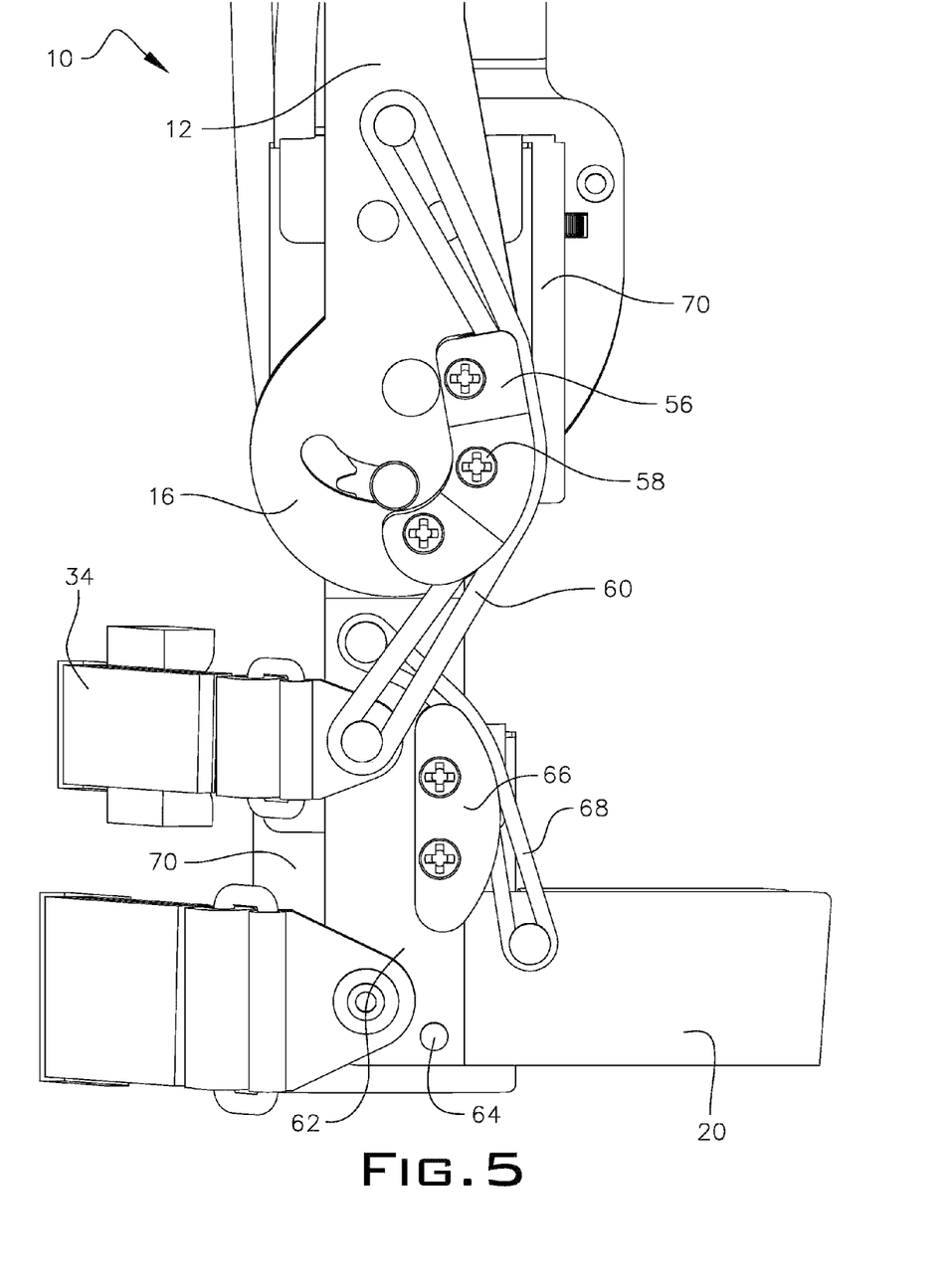
FIG. 5 is a left side view of the knee orthosis of the present invention illustrating a polycentric hinge and deflection guide of a left side vertical strut and a left side shin cuff hinge.

Referring now to FIG. 5, it is shown that polycentric hinge 16 includes a deflection guide 56, which optionally includes a plurality of setting blocks 58 and a tensile member 60. The tensile member 60 is attached at opposed ends to knee orthosis 10, and stretches over the plurality of setting blocks 58 to provide a force to knee orthosis 10 to assist patients in gait kinetics and musculature exercise. The tensile member 60 may be any component capable of providing a tensile force, including but not limited to one or more elastic bands, o-rings, coil springs, rubber bands, or resilient member.

The deflection guide 56 acts to keep the tensile member 60 some distance away from the axis of rotation of the hinge 16/18. If the tensile member is allowed to move beyond the hinge 16/18 it either becomes ineffective by providing no extension force, or counter-productive by creating a bending, rather than extending, force.

Nothing herein limits the use of only one deflection guide 56, nor does anything herein limit which side deflection guide 56 is employed in the case that only one deflection guide 56 is employed with knee orthosis 10, as shown in the preferred embodiment.

When a strut 12/14 is bent across hinge 16/18, the deformation/elongation of tensile member 60 provides a force to aid in leg extension, or straightening of the knee joint. In some examples, the tensile member 60 is in a contracted or relaxed state when the strut 12/14 is in a generally parallel relationship, and in an extended or stretched state when the strut 12/14 is in a generally bent. As a result of creating a force that aids in leg extension, the tensile member 60 acts as a motion accelerating mechanism. The force that is created by the tensile member 60 is either a constant force regardless of length through use of a constant force spring or equivalent, or more commonly the force increases as the tensile member 60 experiences greater deformation/elongation.

Figure 6:
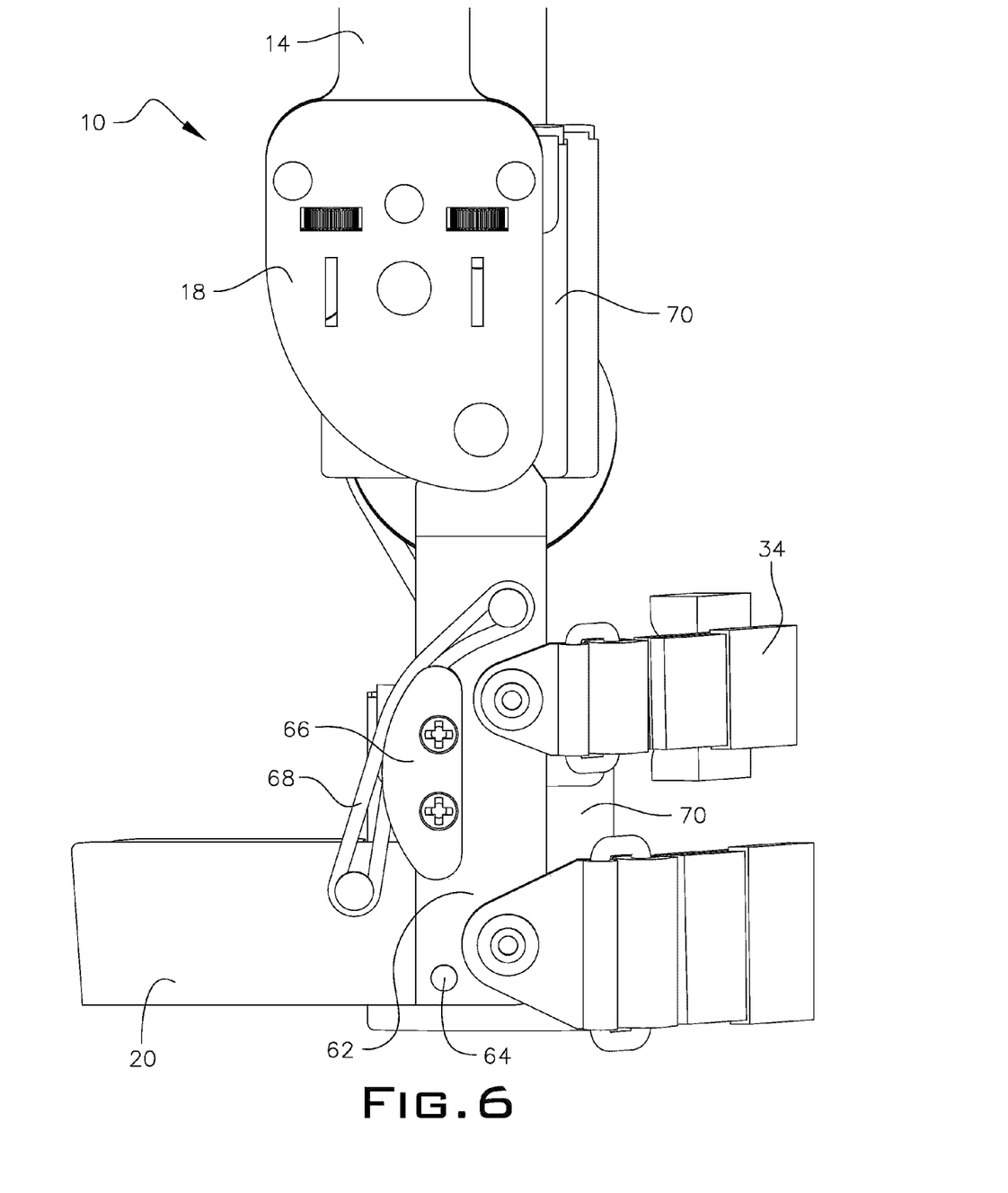
FIG. 6 is a right side view of the knee orthosis of the present invention illustrating a uni-centric hinge and of a right side vertical strut and a right side shin cuff hinge.
Figure 7:
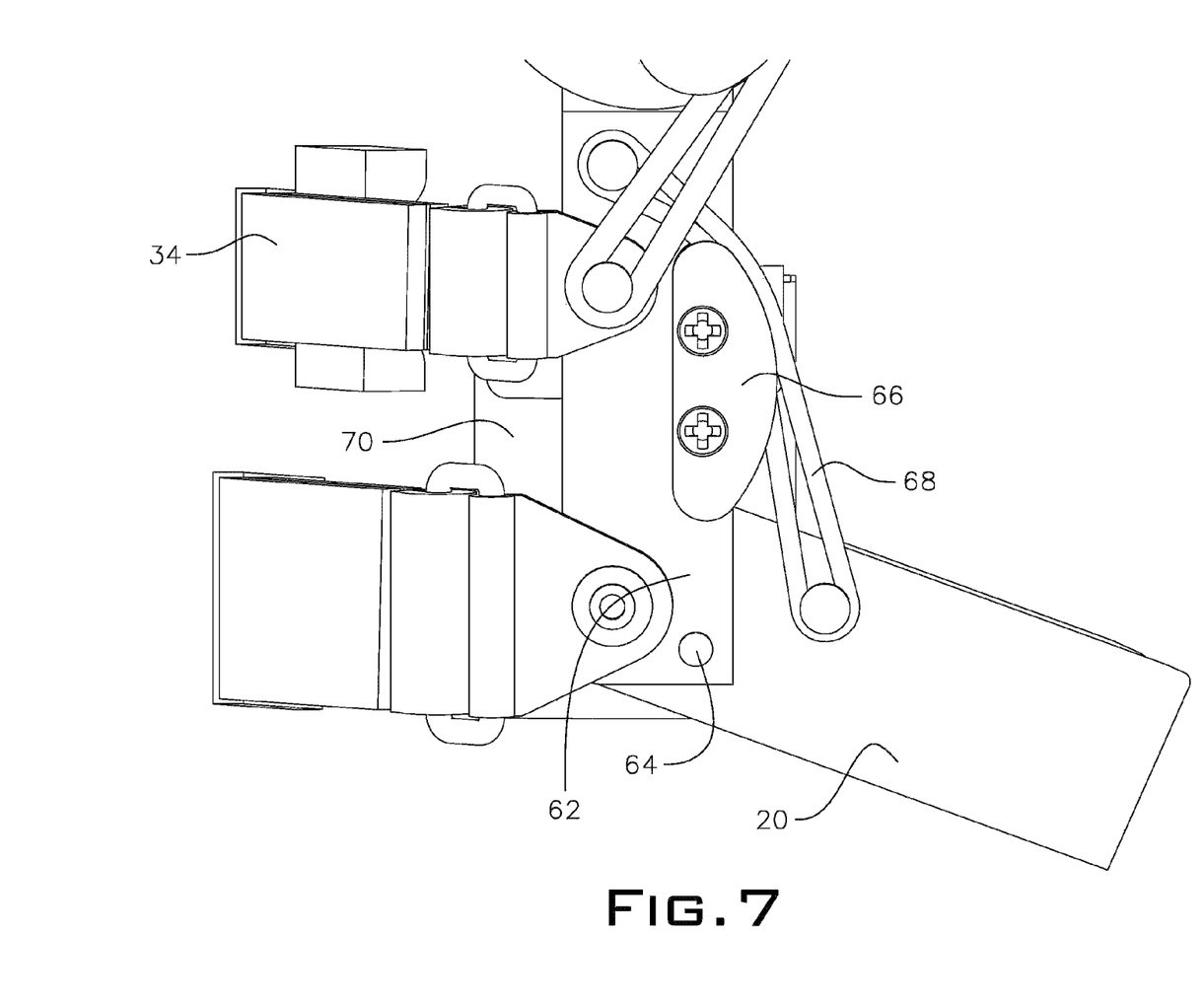
FIG. 7 is a left side view of the knee orthosis of the present invention illustrating how the shin cuff angles downwardly away from a horizontal plane.

Referring now to both FIGS. 5 and 6, it is shown that knee orthosis 10 also includes a shin cuff hinge assembly 62 on both left and right lower ends, 26 and 28, of left and right vertical struts, 12 and 14. Each shin cuff hinge assembly 62 contains a pivoting axis 64, a setting block 66 and a shin tensile member 68, attached at opposed ends to knee orthosis 10, for stretching over setting block 66. The shin tensile member 68 may be any component capable of providing a tensile force, including but not limited to one or more elastic bands, coil springs, rubber bands, or resilient member. As shown in FIG. 7, shin cuff 20 pivots downwardly about both axis 64, so that shin cuff 20 reduces the pressure applied against the shin of the patient when he walks, flexes his knee or squats down. Shin tensile member 68 provides a means to return shin cuff 20 to its normal resting state when the patient ceases to walk, flex his knee or squat down.

Referring back to FIGS. 1 and 2, it can be seen that a plurality of air bladders 70 are employed along inner surfaces of the left and right vertical struts 12 and 14. Bladders 70 are attached to knee orthosis 10 by hook and loop material and are therefore removably attachable. Although only four air bladders 70 are shown, nothing herein limits the use of more or less than four bladders. For example, in an alternate embodiment, six air bladders 70 are employed to provide corrective and therapeutic force to the knee joint area at the knee joint on both sides, above the knee joint on both sides and below the knee joints on both sides.

Figure 8:
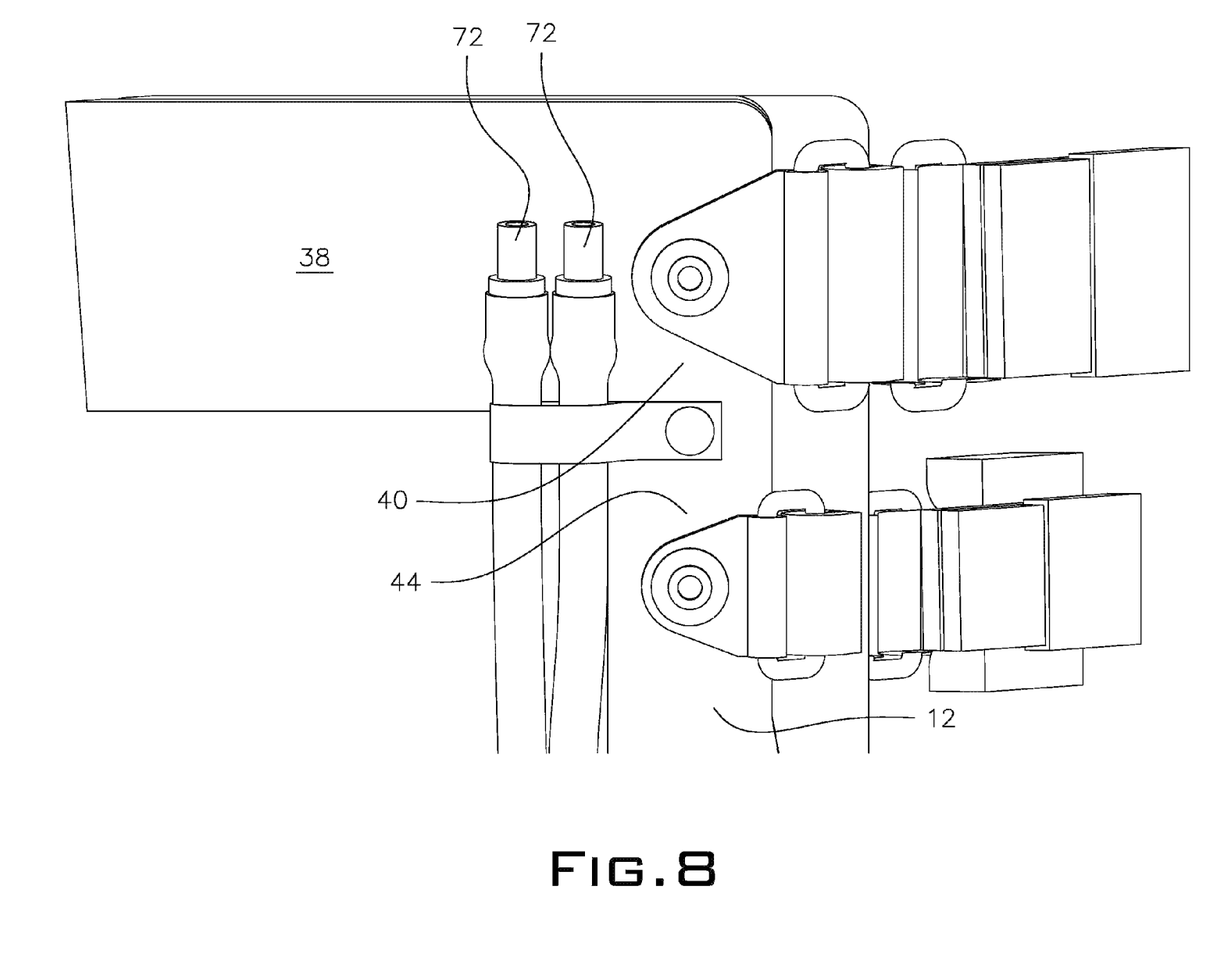
FIG. 8 illustrates the inflation tubes of the air bladders used in conjunction with knee orthosis of the present invention as the therapeutic and corrective force employed to the knee joint area and the surrounding leg musculature.

Referring to FIG. 8, a set of inflation tubes 72 are shown, which are used to inflate or deflate air bladders 70 depending on therapist or patient preferences.

In the preferred embodiment, knee orthosis 10 is made from highly pliable, semi-rigid materials that permit knee orthosis 10 to bend, flex, and move with the movements of the patient, but all the while maintaining the knee in a completely stabilized and immobile state. However, nothing herein limits the use of more rigid, less pliable materials if necessary.

Although not shown, the upper thigh cuff can also employ a pair of hinges located proximal to the thigh cuff opposed ends and left and right vertical strut upper end portions for permitting the thigh cuff to pivot upwardly away from a thigh of a person wearing the knee orthosis when a person flexes the knee or performs any other motion thereby reducing or eliminating unwanted pressure that is usually applied to the thigh of a patient of a person when they flex the knee, walk or squat. The thigh cuff can pivot upwards of 60-75 degrees or more. The present invention can employ a hinged shin cuff, a hinged thigh cuff, or both a hinged shin and hinged thigh cuff.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

The invention claimed is:
1. A knee orthosis device comprising:
a) two vertical struts, adapted to be positioned on opposed sides of a knee joint in a generally parallel relationship, each of the vertical struts having a hinge member, each of the vertical struts having a proximal section and a distal section, the proximal section having a proximal end, the distal section having a distal end;
b) an upper thigh cuff attached at opposed ends to the proximal ends of each of the vertical struts:
c) a lower shin cuff attached at opposed ends to the distal ends of each of the vertical struts; and
d) a first swing assist assembly containing at least one tensile member located on one of the two vertical strut hinge members, a first end of the tensile member connected to the proximal half of the one of the two vertical struts, a second end of the tensile member connected to the distal half of the same vertical strut, the first swing assist assembly acting to straighten one of the two vertical struts;
e) wherein the at least one tensile member is an elastic loop without terminations, the elastic loop adapted to store and release energy created by a user's gait.
2. The knee orthosis of claim 1, wherein the lower shin cuff is attached at opposite ends to the distal portions of the two vertical struts by a pair of pivots, each pivot of the pair of pivots located at the distal end portion of each of the two vertical struts.

3. The knee orthosis of claim 2, further comprising one or more shin cuff elastic members connecting the shin cuff with one or both of the two vertical struts.

4. The knee orthosis of claim 1, further comprising a second swing assist assembly containing a second tensile member on the vertical strut opposing the first swing assist mechanism, a first end of the second tensile member connected to the proximal half of the one of the two vertical struts, a second end of the second tensile member connected to the distal half of the same vertical strut, the swing assist assembly acting to straighten one of the two vertical struts.

5. The knee orthosis of claim 4, wherein the at least one tensile member always acts to extend the knee orthosis, regardless of an angle of flexion created across the hinge between the respective proximal section and distal section of one vertical strut.

6. The knee orthosis of claim 1, wherein the first swing assist assembly includes a deflection guide that prevents the at least one tensile member from crossing an axis of either hinge member.

7. The knee orthosis of claim 1, wherein the at least one tensile member is adapted to aid the extension of the knee joint by continuously creating a force that acts to straighten, or extend, the knee orthosis.

8. The knee orthosis of claim 1 further comprising a plurality of air bladders employed along inner surfaces of one or both of the vertical struts, the air bladders configured to apply corrective and therapeutic force to the knee joint on both sides.

9. The knee orthosis of claim 1, wherein the first swing assist assembly and at least one tensile member are integral to one of the two vertical strut hinge members.

10. The knee orthosis of claim 1, wherein the elastic loop has an O-shaped cross section.

11. A knee orthosis device comprising:
a) a first and second vertical strut adapted to be positioned on opposing sides of a knee joint and arranged in a generally parallel relationship, the first vertical strut having a proximal section and a distal section, the second vertical strut having a proximal section and a distal section;
b) the first vertical strut having a first hinge member, the first hinge member connecting the proximal section and the distal section;
c) the second vertical strut having a second hinge member, the second hinge member connecting the proximal section and the distal section;
d) opposed ends of an upper thigh cuff attached to the proximal section of the first vertical strut and the proximal section of the second vertical strut;
e) opposed ends of a lower shin cuff attached to the distal section of the first vertical strut and the distal section of the second vertical strut; and
f) a motion accelerating mechanism for encouraging a rate of extension of the knee orthosis device, said motion accelerating mechanism including at least one tensile member generating a force proportional to an angle of flexion between the distal section and the proximal section of either of the two vertical struts; and
g) wherein the tensile member is a single loop without ends, and acts alone to store and release energy created by a user's gait.

12. The knee orthosis of claim 11, further comprising a deflection guide adapted to maintain the at least one tensile member on an anterior side of the knee orthosis, preventing the at least one tensile member from crossing an axis of either the first hinge member or the second hinge member.

13. The knee orthosis of claim 12, wherein the lower shin cuff is rotatable about a pair of pivots, adapted to allow an inner surface of the shin cuff to remain substantially parallel to a shin of a person wearing the knee orthosis during motion.

14. The knee orthosis of claim 13, further comprising one or more shin cuff elastic members connecting the shin cuff with one or both of the vertical struts.

15. The knee orthosis of claim 12, wherein the motion accelerating mechanism is integral to either the first hinge member or the second hinge member.

16. The knee orthosis of claim 11 further comprising a plurality of adjustable air bladders employed along inner surfaces of one or both of the first and second vertical struts, the adjustable air bladders configured to apply varying amounts of corrective and therapeutic force to the knee joint on both sides, the varying amounts of force adjustable based on air pressure.

17. The knee orthosis of claim 11, wherein the at least one tensile member is a loop.

18. The knee orthosis of claim 11, wherein the at least one tensile member is has an O-shaped cross section.

19. A knee orthosis device comprising:
a) a first and second vertical strut adapted to be positioned on opposing sides of a knee joint, each of the first and second vertical struts having a proximal half and a distal half;
b) a first hinge member connecting the proximal half of the first strut to the distal half of the first strut; a second hinge member connecting the proximal half of the second strut to the distal half of the second strut;
c) a first end of the proximal half of the first strut attached to a point of an upper thigh cuff and the first end of the proximal end of the second strut attached to an opposing point of the upper thigh cuff;
d) a second end of the distal half of the first strut attached to a point of a lower shin cuff and the second end of the distal end of the second strut attached to an opposing point of the lower shin cuff; and
e) a tensile member connected at one end to the proximal half of the first vertical strut and connected on a second end to the distal half of the first vertical strut, the tensile member in a contracted state when the proximal half and the distal half of the first vertical strut is in a parallel relationship, and in an extended state when the proximal half and distal half of the one or more vertical struts is in a bent relationship and
f) wherein the tensile member is a continuous loop, the continuous loop having a first end and a second end, the first end of the continuous loop connected to the second end of the continuous loop, and the tensile member is configured to increase and decrease length in order to store and release energy created by a user's gait, without the use of a spring.

20. The knee orthosis of claim 19, further comprising:
a) a second tensile member connected at one end to the proximal half of the second vertical strut and connected on a second end to the distal half of the second vertical strut, the second tensile member in a contracted state when the proximal half and the distal half of the first vertical strut is in a parallel relationship, and in an extended state when the proximal half and distal half of the one or more vertical struts is in a bent relationship.

* * * * *